US006868634B2

(12) United States Patent
Parker

(10) Patent No.: US 6,868,634 B2
(45) Date of Patent: Mar. 22, 2005

(54) INSECT RESISTANCE MANAGEMENT IN AGRICULTURAL APPLICATIONS

(75) Inventor: Charles D. Parker, Ridgeland, MS (US)

(73) Assignee: Mississippi State University, Mississippi State, MS (US)

( * ) Notice: Subject to any disclaimer, the term of this patent is extended or adjusted under 35 U.S.C. 154(b) by 0 days.

(21) Appl. No.: 10/263,780

(22) Filed: Oct. 4, 2002

(65) Prior Publication Data

US 2003/0084606 A1 May 8, 2003

Related U.S. Application Data

(60) Provisional application No. 60/326,687, filed on Oct. 4, 2001.

(51) Int. Cl.$^7$ .............................................. A01B 79/00
(52) U.S. Cl. ....................................................... 47/58.1
(58) Field of Search ........................................... 47/58.1

(56) References Cited

PUBLICATIONS

Stadelbacher et al., "Heliothis Populations and Wild Host Plans in the Southern U.S.", Feb. 1986, Southern Cooperative Series, pp. 54–74.*
"EPA and USDA Position Paper on Insect Resistance Management in Bt Crops", EPA, Office of Pesticide Programs, (1999).
Caprio, M., "Bacillus thuringiensis Gene Deployment and Resistance Management in Single– and Multi–tactic Environments", Biocontrol Science and Technology, 4, 487–497 (1994).
Craig, C., et al., "Use of Alternate Hosts As a Trap for Tarnished Plant Bugs and a BT–Susceptible Tobacco Budworms", Cotton Insect Research and Control Conference, 1999 Beltwide Cotton Conferences, 1056–1061(1991).
Fischoff, D., "Management of Lepidopteran Pests With Insect Resistant Cotton: Recommended Approaches", Cotton Insect Research and Control Conference, 1992 Beltwide Cotton Conferences, 751–753 (1992).
Gould, F., "Evolutionary Biology and Genetically Engineered Crops, Consideration of Evolutionary Theory Can Aid in Crop Design", Bioscience, 38, 1, 26–33 (1988).
Gould, F., et al., "Selection and Genetic Analysis of a Heliothis virescens (Lepidoptera: Noctuidae) Strain With High Levels of Resistance to Bacillus thuringiensis Toxins", Journal of Economic Entomology, 88, 6, 1545–1559 (1995).
"An Evaluation of Insect Resistance Management in Bt Field Corn: A Science–Based Framework for Risk Assessment and Risk Management, Report of an Expert Panel", Int'l. Life Sciences Institute, Health and Environmental Sciences Institute (1998).
Mallet, J., et al., "Preventing Insect Adaptation to Insect–Resistant Crops: Are Seed Mixtures or Refugia the Best Strategy?", Proc. R. Soc. Lond. B, 250, 165–169 (1992).

(List continued on next page.)

Primary Examiner—Bruce R. Campell
Assistant Examiner—S. B. McCormick-Ewoldt
(74) Attorney, Agent, or Firm—Steven B. Kelber; DLA Piper Rudnick Gray Cary US LLP

(57) ABSTRACT

A method of providing a refuge for caterpillar larvae, which are susceptible to plants expressing delta endotoxin of Bacillus thuringiensis so as to delay and possibly prevent the susceptible species from developing resistance to the toxin. Also provided is a method of cultivating paulownia trees so as to provide an effective refuge for the susceptible caterpillar larvae.

18 Claims, 4 Drawing Sheets

OTHER PUBLICATIONS

Matten, S., "EPA Regulation of Transgenic Pesticidal Crops and Insect Resistance Management for B.T. Cotton", Biotechnology Special Session, 2000 Beltwide Cotton Conferences, 71–75 (2000).

McGaughey, W., "Managing Insect Resistance to *Bascillus thuringiensis* Toxins", Science, 258, 1451–1455 (1992).

Parker, C., "Temporal Distribution of Heliothines in Corn-Cotton Cropping Systems of the Mississippi Delta and Relationships to Yield and Population Growth", Dissertation, Mississippi State University 116 pgs. (2000).

Snow, J. et al., "Seasonal Host Activity of the Bollworm and Tobacco Budworm During 1963 in Northeast Mississippi", Mississippi Agricultural Experiment Station Bulletin 712 (1965).

Snow, J., et al., "*Geranium carolinianum* as an Early Host for *Heliothis zea and H. virescens* (Lepidoptera: Noctuidae) in the Southeastern United States, With Notes on Associated Parasites", Annals of the Entomological Society of America, 59, 3, 506–509 (1966).

"Theory and Tactics of *Heliothis* Population Management: 1– Cultural and Biological Control", Southern Cooperative Series, Bulletin No. 316 (1986).

Kays, J., et al., "How to Produce and Market Paulownia", Univ. of Maryland, Coop. Ext. Ser., Bulletin 319 (1997).

IRM Guide 2002, "Insect Resistance Management—The Cotton Grower's Guide to Preserving Technology by Protecting Against Insect Resistance", Monsanto Company (2002).

* cited by examiner

INSECT RESISTANCE MANAGEMENT IN AGRICULTURAL APPLICATIONS

This application claims priority from U.S. Provisional Application Ser. No. 60/326,687 filed Oct. 4, 2001. The entirety of that provisional application is incorporated herein by reference.

BACKGROUND OF THE INVENTION

1. Field of the Invention

The invention relates to a method for insect resistance management in agriculture applications. More particularly, this invention pertains to providing a refuge for pest insects adjacent to plantings of genetically modified plants that produce insecticidal proteins of *Bacillus thuringiensis* such as BT-cotton, BT-corn, and BT-potatoes (BT Crops), said refuge providing a method for delaying, or possibly preventing said pests from developing resistance to the *Bacillus thuringiensis* protein.

2. Background of the Technology

The introduction of transgenic cotton plants expressing endotoxin derived from *Bacillus thuringiensis* Berliner (BT cotton) has greatly aided producers in maintaining control of *Heliothis virescens* larvae (tobacco budworm) and *Helicoverpa zea* larvae (bollworm), although to a lesser degree. BT cotton plants provide season long expression of the insecticidal toxins which has raised concerns about resistance development.

According to a United States Environmental Protection Agency (EPA) and United States Department of Agriculture (USDA) position paper on Resistance Management[1], the EPA and USDA "generally support the following strategy to manage the development of pest resistance to BT toxins expressed in crops. That is, a structured refuge/high dose strategy should be employed for susceptible pests within the current understanding of the technology. The presence of an effective structured refuge, in combination with a high dose expression level of the BT toxin, has the potential to delay the development of resistance in pests. Refuges are non-BT host plants that are managed to provide sufficient susceptible adult insects to mate with potential BT-resistant adult insects to dilute the frequency of resistance genes. The 1998 SAP subpanel on BT crop resistance management suggested that production of 500 susceptible adults in the refuge should be available for mating with every potentially resistant adult in a BT field (assuming a resistance allele frequency of 5×10−2) (Final Report of the Subpanel on *Bacillus thuringiensis* (BT) Plant-Pesticides and Resistance Management, February, 1998 (186 kb, PDF).[1] Several strategies have been discussed (Fischoff 1992, McGaughey and Whalon 21992, Mallet and Porter 1992, Caprio 1994), but the current strategy recommends the use of plants with high dose expression and the provision of an external refuge in close proximity to the transgenic plants (ILSI HESI 1998). Under the current strategy, producers using the BT cotton technology are allowed two possible options (S. Matten 2000). 1) For every 100 acres, Non-BT cotton must be planted on 20% of the acreage within one mile of the transgenic field, and the non-BT cotton may be treated with insecticides except for BT insecticide products. 2) For every 100 acres, Non-BT cotton must be planted on 3.8% of the acreage with in one mile from BT fields, but the refuge cannot be treated with any insecticide having activity on lepidopteran larvae. Non-BT cotton has been adopted as the refuge because it will be temporarily similar to the BT cotton and can serve as a refuge for the entire cotton production season. This option was subsequently revised (IRM Guide 2002) to provide a 5% unsprayed refuge instead of 3.8%.

Other hosts for *Heliothis virescens* and *Helicoverpa zea* have been reported (Quaintance and Brues 1905, Snow and Brazzel 1965, Snow et al. 1966, Stadelbacher et al. 1986), but many of these hosts are short lived. Other studies have explored the possibility of planting identified hosts to serve as a refuge for BT cotton, but these planting were comprised mainly of plants considered weeds in the cotton production system (Craig et al. 1999). Although the concept of using such plants as a refuge is valid, it would be easier to promote using alternative refuge plants that are not considered weed species. *Paulownia* was reported as a host of *Heliothis virescens* in a graduate student dissertation (Parker 2000), but the production of larvae per acre was not considered to be sufficient for refuge use.

*Paulownia* is a rapid growing tree introduced to the United States from China over 150 years ago (Kays et al. 1997). There are several species but *Paulownia tomentosa* is probably the most widespread. Others include *Paulownia elongata, Paulownia fortunei,* and *Paulownia catalpafolia*. *Paulownia* has a sparse distribution across the cotton belt, but in recent years has become an interest of some tree production farms. Parker (2000) reported that the plant spacing required for the tree production limited the per acre production of larvae although larvae were utilizing the *paulownia* for the entire cotton production season.

What is needed in the cotton farming industry is a refuge crop that will provide adequate refuge for *Heliothis virescens* larvae and *Helicoverpa zea* larvae and other cotton pests without requiring cotton farmers to sacrifice part of their yield or a large portion of valuable agricultural land.

SUMMARY OF THE INVENTION

The inventor has solved the above problem by discovering that it is possible to cultivate *paulownia* so as to produce more heliothine larvae (*Heliothis virescens* and *Helicoverpa zea*) than cotton produces and thus to provide a refuge, which alleviates concerns that these and other cotton pests will quickly develop resistance to BT toxins produced by BT cotton.

The invention relates to a method for insect resistance management in agriculture applications comprising a copse of trees to serve as the refuge for insects. In one embodiment of the invention the trees are from the *Paulownia* species comprising *Paulownia elongota, Paulownia tomentosa,* and *Paulownia fortunei.*

It is an object of this invention to provide a refuge for pest insects in proximity to plantings of BT crops comprising a copse of trees such as various species of *Paulownia.*

It is a further object of this invention to provide a method to optimize the number and density of pest insects that can be sustained in the refuge by trimming and pruning the trees and by planting the trees close together which individually and collectively increases the density of foliage which sustains the insects.

In is a further object of this invention to provide a refuge for pest insects including *Helicoverpa zea* (cotton bollworm and corn ear worm), *Leptinotarsa decemlineata* (Colorado potato beetle), *Ostrinia nubilalis* (European corn borer), *Spodoptera frugiperda* (fall armyworm), *Pectinophora gossypiella* (pink bollworm), *Diatraea crambidoides* (southern corn stalk borer), *Diatraea grandiosella* (southwestern corn borer), lepidopteran larvae, and tobacco budworm.

Figure 2:
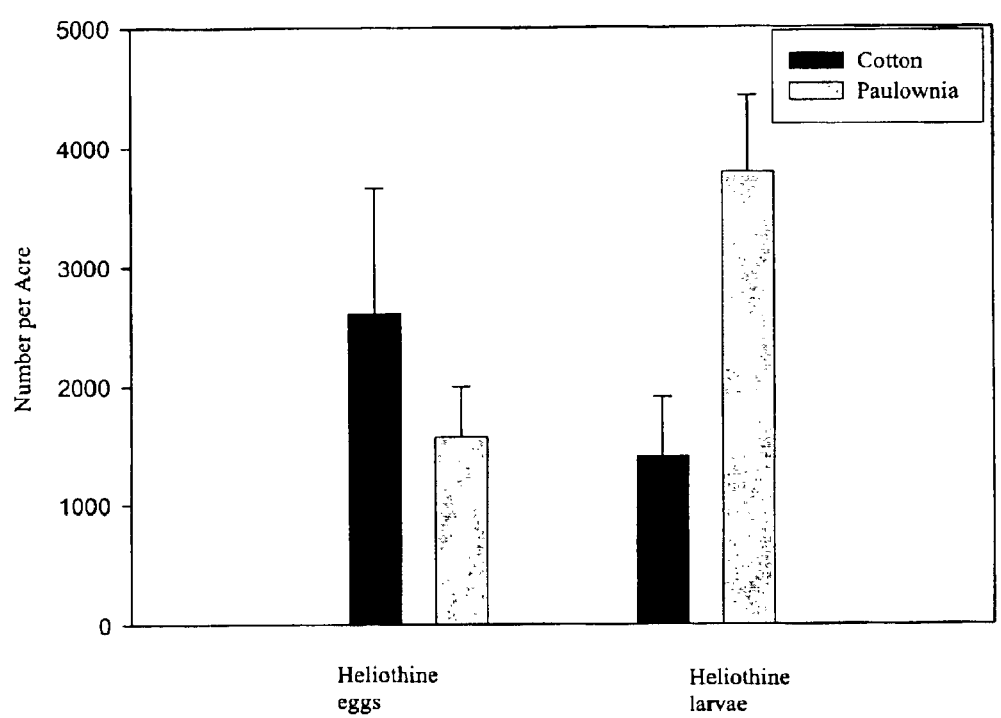

FIG. 2 shows mean (SEM) number of heliothine (*Heliothis virescens* and *Helicoverpa zea*) eggs and larvae per acre of *paulownia* and cotton for all sample dates during the test period.

Figure 3:
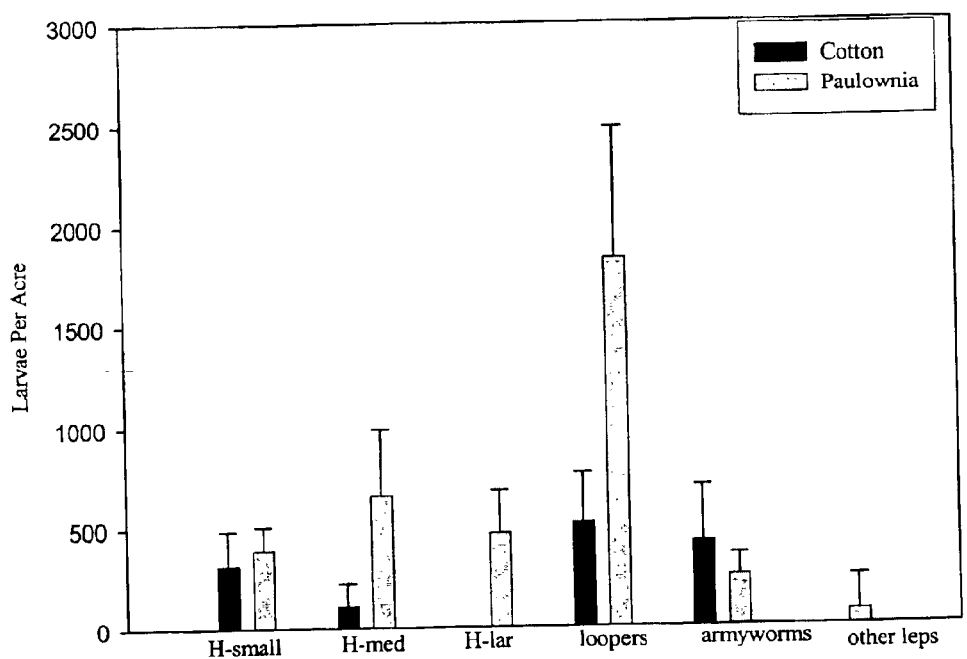

FIG. 3 shows mean (SEM) number of small (H-small) medium (H-med), and large (H-lar) heliothine larvae (*Heliothis virescens* and *Helicoverpa zea*), number of loopers, armyworms, and other lepidopteran larvae across all sample dates for cotton and *paulownia* during the test period.

Figure 4:
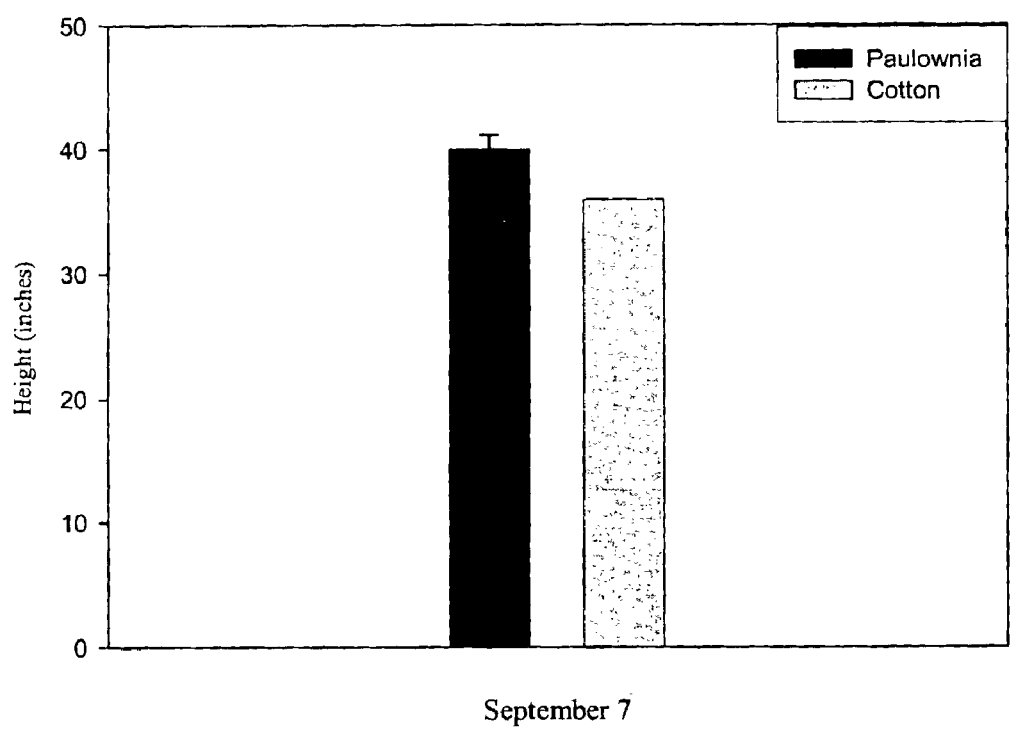

FIG. 4 shows comparative mean (SEM) height in inches for *paulownia* and cotton at a point in time during the test period.

DETAILED DESCRIPTION

The inventor has discovered that a refuge can be provided for *Heliothis virescens, Helicoverpa zea* and other cotton pests that slows the development of resistance to BT in pests without sacrificing portions of the cotton crop or large portions of valuable land.

The following described refuge option, developed by the inventor, has surprisingly managed to achieve this goal. Certain basic factors must be taken into account in the development of an effective refuge. The placement and size of the structured refuge employed should be based on the existing target pest biology data (e.g., larval and adult movement, mating and ovipositional behavior, fecundity). The refuge should be planted with an agronomically similar hybrid and as close as possible to, and at the same time as, the BT crop. Refuge size should be adjusted or alternative control measures proposed if there is a lack of a high dose for a particular target pest.

In the development of refuge options, the following considerations should be made. First, the applicability of an in-field versus external refuge for each target (susceptible) pest should be evaluated based on larval and adult movement, ovipositional and mating behavior. The proximity of an external refuge must be within the normal adult flight range to mating/ovipositional habitats. If there are multiple pests, the structured refuge options should be inclusive of all potential target (susceptible) pests. If there are regional pest considerations, the structured refuge options should reflect these considerations. Therefore, structured refuge options should be designed within the feasibility and current understanding of the technology to address all of the target pest species including the pest with the greatest susceptibility to the BT toxin.

In accordance with the present invention structured refuge options can be designed with a high degree of grower adoption in mind. An important consideration in designing a refuge is whether there is a single dominant pest for a particular region or locality and whether there is a high dose of toxin produced. In addition, refuge strategies designed in accordance with the present invention can take into consideration whether there are stacked genes versus single genes to control the same target pests or different target pests. Resistance management strategies such as the structured refuge of the present invention can be designed with flexibility to accommodate rapidly changing technology (e.g., gene stacking or adding additional BT proteins), new research data, and improved understanding of resistance management.

A structured refuge designed in accordance with the present invention will provide sufficient susceptible adult insects to mate with potential BT-resistant adult insects to dilute the frequency of resistance genes. Past efforts to achieve an effective refuge strategy for resistance control in pests management have led to controversy over the size, structure, and deployment of non-BT crop refuges and how they should be implemented on a regional basis.

As discussed earlier, the conventionally recommended alternative resistant management options have required growers to plant 80% of their land to BT cotton, but the remaining 20% must be planted to non-BT cotton or, in the second option, to plant 95% of the acreage to BT cotton, but 5% of the acreage must be planted to non-BT cotton. Both options require the grower to sacrifice a percentage of his production acreage to the effects of pest insects. The present invention provides an economical means of providing an effective refuge without the conventional large sacrifices of crop production and loss of agricultural land use.

The present invention has provided a refuge which uses *Paulownia* species of trees as a suitable host for pest insects, which attack cotton, such as *Heliothis virescens* (tobacco budworm), a major caterpillar pest. Plantings of the *Paulownia* trees in a copse, which can be easily managed year to year, provides an excellent structured refuge on less acreage (considerably less than 5%) while increasing the number of susceptible pest insects such as lepidopteran larvae.

The *Paulownia* tree originated in China and was introduced to the U.S. as an ornamental plant. In recent years, some tree production farms have planted *Paulownia* for commercial production but it has not found use in resistance management applications. The *Paulownia elongota* is a rapid growing tree that will flower in the early spring. It can be readily maintained and pruned to limit it growth.

According to the present invention, 95–99½ acres of a BT-crop are planted in a 100 acre field. The remaining ½ to 5 acres are planted with *Paulownia elongota* trees spaced about 3 feet apart and maintained at a height of about 4 feet through routine trimming and pruning. While this is the preferred embodiment, it is within the concept of the invention to provide a *paulownia* refuge planted at varying distances up to 20 feet apart and having a height up to 15 feet or more. Taller more widespread trees would necessarily require more acreage from the field; and under optimum conditions be a less desirable option. However in areas of varying types of terrain where not all of the acreage is cultivatable, the spacing and height of the *paulownia* trees can be expected to vary from the preferred embodiment but still fall within the scope thereof.

The *paulownia* trees can be maintained from year to year or replaced as needed. The trees can be grouped into a single area, or in any manner consistent with establishment of a structured refuge in accordance with EPA guidelines[1]. Fields of other sizes may be planted according to the relative percentages outlined above. A refuge prepared in accordance with the present invention can employ only 5% of the available agricultural field although the present invention can be effective with 4%, 3%, 2%, 1%, or even as little as ½% of the land devoted to refuge plant production.

Alternatively, trees can be grown up to their natural height and planted at larger spacings, but a larger refuge area will be required to support the same number of pest insects due to the lower foliage density. However, in areas with difficult terrain, it may be more advantageous to plant such a larger area as such terrain may not be suitable for BT-crop production.

EXAMPLES

Initial studies were conducted on the Brown Loam Experiment Station of Mississippi State University in Learned, Miss. The treatments were *Paulownia elongota* and nectaried cotton. Each plot was planted on 38 inch row centers, 16 rows×50 linear feet. Cotton was planted at normal agronomic rates (approximately 3 plants per row feet). The seedlings trees were planted approximately 3 feet apart within rows. The data that was obtained from a sampling of the plot on a single day during the test period is shown in Table 1. The results for the same sampling in Table 2 are in per acre terms.

TABLE 1

|  | Paulownia | Cotton |
| --- | --- | --- |
| Plants sampled | 100 | 75 |
| Total Helio eggs | 0 | 0 |
| Total Helio larvae | 122 | 1 |
| Small Helio larvae | 18 | 1 |
| Medium Helio larvae | 62 | 0 |
| Large Helio larvae | 42 | 0 |
| Loopers | 142 | 4 |
| Armyworms | 18 | 4 |
| Other Lepidopterans | 3 | 0 |

TABLE 2

|  | Paulownia | Cotton |
| --- | --- | --- |
| Total Helio eggs | 0 | 0 |
| Total Helio larvae | 5594 | 521 |
| Small Helio larvae | 825 | 521 |
| Medium Helio larvae | 2842 | 0 |
| Large Helio larvae | 1925 | 0 |
| Loopers | 6511 | 2085 |
| Armyworms | 825 | 2085 |
| Other Lepidopterans | 137 | 0 |

Extensive studies were conducted, which compared untreated Non-BT cotton to untreated *paulownia* with regards to production of lepidopteran larvae. *Paulownia elongata* seedlings in 2×2×3 inch plastic cell trays were purchased from Carolina Pacific International, Inc. (Lenox, Ga.). On July 10, four replicates of the two treatments (*paulownia* and cotton) were planted. Prior to planting, all plots were disked equally to prepare the seedbed. The *paulownia* plots were 50 ft in length by 16 rows wide (38 inch centers), and plants were spaced 38 inches apart within rows. *Paulownia* seedlings were hand planted and one fertilizer tablet (20N-10P-5K) purchased from Carolina Pacific International was placed approximately 2 inches to the side of the seedling. Cotton plants ('Suregrow 521R') were planted the same day using a vacuum planter. The cotton plants were planted at normal field spacing (3 to 4 plants per linear foot of row.).

*Paulownia* plots were flood irrigated for one week to prevent seedlings from dying. This is a normal practice for *paulownia* transplants. Plants were monitored on a weekly basis for heliothine eggs and/or larvae, and other lepidopteran larvae. Initial data included number of eggs and/or larvae visually observed per 25 plants. After initial observations were made, the inventor determined that the size of the larvae observed should also be considered. Therefore the visual observations were modified to include the number of small (less than ¼ inch), medium (¼–½ inch), and large (greater than ½ inch) heliothine larvae, the number of loopers (*Trichoplusia ni* and *Pseudoplusia includens*), the number of armyworms (Pseudaletia and Spodoptera spp.), and the number of other lepidopteran larvae. Table 3 provides the mean (SEM) number of heliothine eggs, small, medium, large, and total heliothine larvae, armyworm larvae, shinx eggs and larvae, and looper larvae per acre of each species of *Paulownia*.

TABLE 3

|  | Catalpifolia Mean(SEM) | Elongata Mean(SEM) | Fortunei Mean(SEM) | Tomentosa Mean(SEM) |
| --- | --- | --- | --- | --- |
| Heliothine eggs | 787(346) | 886(519) | 1082(551) | 1181(598) |
| Heliothine small | 984(314) | 688(252) | 1279(362) | 590(236) |
| Heliothine medium | 1771(661) | 1082(378) | 1476(362) | 2363(834) |
| Heliothine large | 3050(928) | 2263(67) | 1968(583) | 2656(567) |
| Heliothine toal | 5805(1165) | 4035(992) | 4723(614) | 5609(1023) |
| Armyworm larvae | 393(173) | 295(220) | 295(157) | 492(236) |
| Shinx eggs | 1070(441) | 1673(583) | 1771(945) | 2263(1055) |
| Shinx larvae | 0(0) | 98(94) | 295(157) | 492(315) |
| Looper larvae | 17319(9211) | 18303(9573) | 21157(10312) | 33063(15004) |

No significant differences were detected between paulownia species for any variable by least means significant test ($p \leq 0.05$).

no signicant differences were delected between *paulownia* species for any variable by least means significant test ($\leq 0.05$).

On September 7 a measurement of height (in inches) was obtained from 25 plants in each plot of *paulownia* and cotton. The data were recorded and analyzed for the visual observations of 25 plants per plot. The data were analyzed by ANOVA with means separated by Fisher's Protected LSAD. Resulting means and standard errors were converted to a per acre basis for both the cotton and *Paulownia* treatments.

Figure 1:
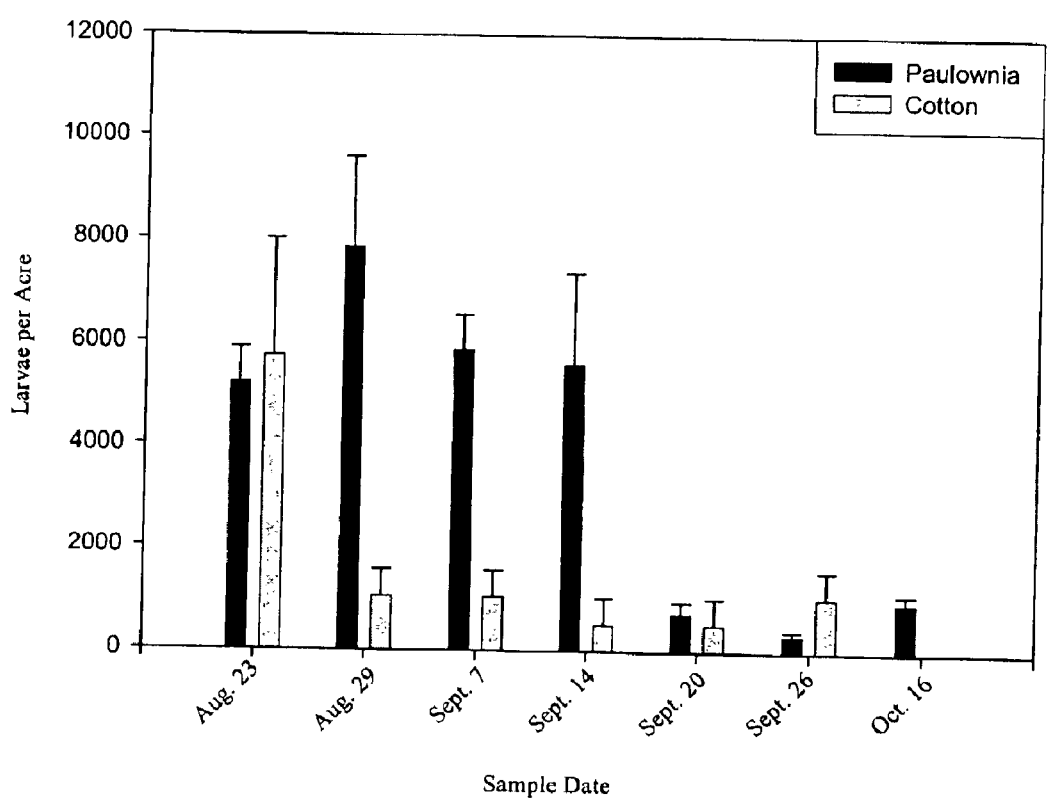
FIG. 1 shows the mean (Standard Error of the Mean (SEM)) number of Heliothine (*Heliothis virescens* and *Heli-* coverpa zea) larvae per acre observed on *paulownia* and cotton for each sample during the test period.

As shown in FIG. 1, a first sampling on August 23, showed statistically similar numbers of heliothine (*Heliothis virescens* and *Helicoverpa zea*) larvae per acre in cotton and *paulownia*. However, the *paulownia* soon began to grow rapidly. It is believed that the *paulownia* required an adjustment period for the transplanted root system. Approximately one week later, on August 29, the *paulownia* had more heliothine larvae than did the cotton (FIG. 1), a trend that remained for sample dates through September 14. On September 20, larval populations on a per acre basis were low and were equivalent between *paulownia* and cotton. Cotton had more larvae per acre on September 26 although the total population density was relatively low. It is worth noting that most of the cotton planted on normal planting dates had reached maturity by September 26, but the cotton in this study had not reached maturity due to the late planting date (both cotton and *paulowania* are normally planted in early May in Mississippi, Kays et al. 1997). However, *paulowania* continued to attract heliothine larvae into October, which would be after defoliation of cotton in Mississippi. On October 16, no larvae were observed on cotton although larvae were still observed on *paulowania*. The *paulownia* trees continued to grow and stay green until the first frost which could mean an extra generation of larval production in the fall for the *paulownia* trees. During the peak larval number (August 19, September 7, and September 14) the *paulownia* had 7.5, 5.6, and 10.84 times more larvae than the cotton, respectively.

Larvae were collected on two dates (August 30 and September 21) for species identification. On August 30, the mandibles were removed from 10 larvae and examined under a stereoscope for species separation. On September 21, the mandibles were removed from 25 larvae and examined for species separation. Data show that 40% of the larvae on August 30 were *Heliothis virescens* and 60% were *Helicoverpa zea*. Data for September 21 show that 96% of the larvae were *Heliothis virescens* and 4% were *Helicoverpa zea*.

The mean number of total eggs and total heliothine larvae are shown in FIG. 2. More eggs were recorded on cotton than on *paulownia*, however, more larvae were recorded on *paulownia*. This observation could indicate that *paulowania* is a better food source than cotton (resulting in higher survival on *paulownia*). Paulownia did have significantly more heliothine larvae (approximately 2.7 times more larvae) when analyzed across all sample dates (FIG. 2). Once the heliothine larvae data were separated into small, medium, and large heliothine larvae, the data show most heliothine larvae observed on cotton were small larvae (FIG. 3). For all sample dates, *paulownia* and cotton did not differ in terms of small heliothine larvae per acre, but *paulownia* had 6 times more medium sized heliothine larvae, and large larvae were only observed in the *paulownia* plots. In addition, *paulownia* had significantly more looper larvae and other lepitopteran larvae than the cotton (FIG. 3). There were some other lepidopteran larvae recorded on *paulownia*, but not on cotton. Among these other lepidopteran larvae, sphinx larvae were the predominant group.

Although the cotton and *paulownia* were planted at the same time, the *paulownia* had outgrown the cotton by September 7 (FIG. 4). The *paulownia* did have an adjustment period after transplanting but soon made the adjustment and began its rapid growth. The data indicate that *paulownia* has a potential to produce more medium and large larvae as compared to cotton. It seems reasonable to believe this would result in higher numbers of adult moths emerging from *paulownia* as well.

By first frost, the *paulownia* had exceeded 5 feet in height. Preferably, the refuge can be maintained by routine pruning to maintain the height and density of the *paulowania*. The purpose of *paulownia* refuge plantings should not be to produce timber but only to serve as a refuge. Alternatively management of the refuge can include routinely cutting the plants off at ground level and allowing the plants to produce regrowth. This alternative method of maintaining the refuge can require a planting that is large enough to alternate cutting half or more of the planting and allowing regrowth before cutting the remaining portion. This would prevent flowering and insure that seed are not dispersed allowing the escape of the plant species. It should be noted that *paulownia* has been introduced into Mississippi for over 100 years and has not become a weed problem.

Conclusion

The inventor has discovered that *paulownia* can be effectively used as a refuge plant for heliothine larvae as well as other lepidopteran larvae. The refuge of the present invention would exist beyond the cotton-growing season and would require a one-time planting.

References

1) EPA and USDA Position Paper on Insect Resistance Management in BT Crops, May 27, 1999 (minor revisions Jul. 12, 1999).
2) Caprio, M. A. 1994. *Bacillus thuringiensis* gene deployment and resistance management in single- and multi-tactic environments. Biocontrol Sci. and Technol., 4: 487–497.
3) Craig, C., S. Steward, r. Luttrell, J. Robbins, and G. Snodgrass. 1999. Use of alternate hosts as a trap for tarnished plant bugs and a refuge for BT-susceptible tobacco budworms. Pp. 1056–1061. In, P. Dugger and D. Richter (eds.), Proceedings, Beltwide Cotton Conference, National Cotton Council, Memphis, Tenn.
4) Dicke, Stpehen, Forestry Exgtension Specialist, Central Mississippi Res. And Ext. Center, Raymon, Miss.
5) Fischhoff, D. A. 1992. Management of lepidopteran pests with insect resistant cotton: Recommended approaches, pp. 751–753. In, D. J. Herber (ed.), Proceedings, 1992 Beltwide Cotton Production and Research Conference, National Cotton Council, Memphis, Tenn.
6) Gould, F. 1988. Evolutionary biology and genetically engineered crops. Bio-science. 38: 26–33.
7) Gould, F., A. Anderson, A. Reynolds, L. Bumgarner, and W. Moar. 1995. Selection and genetic analysis of a *Heliothis virescens* (Lepidoptera: Noctuidae) strain with high levels of resistance to *Bacillus thuringiensis* toxins. J. Econ. Entomol. 88: 1545–1599.
8) Kays, J., D. Johnson, and J. Stringer. 1997. How to produce and market *paulownia*. Univ. of Maryland, Coop. Ext. Ser. Bull. 319.
9) ILSI health and Environmental Sciences Institute (ILSI HESI). 1998. An evaluation of insect resistance management in BT field corn: A science-based framework for rishk assessment and risk management. Report of an expert panel. ILSI Press, Washington DC.
10) IRM Guide 2002. Insect resistance management: The cotton grower's guide to preserving Technology by protecting against insect resistance. Monsanto Company, St. Louis, Mo.
11) Mallet, J. and P. Porter. 1992. Preventing insect adaption to insect-resistant crops: are seed mixtures or refugia the best strategy? Proc. R. Soc. Lond. 250: 165–169.
12) Matten, S. 2000. EPA Regulation of transgenic pesticidal crops and insect resistance management for B.T. cotton, Pp. 71–78. In, P. Dugger and D. Richter (eds.), Proceedings Beltwide Cotton Conf., National Cotton Council, Memphis, Tenn.
13) McGaughey, W. H. and M. E. Whalon. 1992. Managing insect resistance to *Bacillus thuringiensis* toxins. Science 258: 1451–1455.
14) Parker, Jr., C.D. 2000. Temporal distribution of heliothines in corn-cotton cropping systems of the Mississippi Delta and relationships to yield and population growth. Dissertation, Mississippi State University, 116 pp.
15) Snow, J. W. and J. R. Brazzel. 1965. Seasonal host activity of the bollworm and tobacco budworm during 1963 in Northeast Mississippi. Miss. State Univ., Ag. Exp. Sta. Bull. 712
16) Snow, J. W., J. H. Hamm and J. R. Brazzel. 1966. *Geranium carolinianum* as an early host for *Heliothis zea* and *H. virescens* (Lepidoptera: Noctuidae) in the southeastern United States, with notes on associated parasites. Ann. Entomol. Soc. Am. 59: 506–509.
17) Stadelbacher, E. A., H. M. Graham, V. E. Harris, J. D. Lopez, J. R. Phillips and S. H. Roach. 1986. *Heliothis* populations and wild hosts plants in the southern U.S. In, Theory and Tactics of Heliothis Population Management. Southern Coop. Series Bull. No. 316, Agr. Exp. Sta., Oklahoma State Univ., Stillwater, Okla.

What is claimed is:

1. A method of providing a refuge for caterpillar larvae that are susceptible to plants expressing delta endotoxin of *Bacillus thuringiensis* so as to delay and possibly prevent the susceptible larvae from developing resistance to the toxin, the method comprising:

in a field wherein crop plants are growing that express delta endotoxin of *Bacillus thuringiensis* cultivating a refuge portion of that field containing no crop plants;

planting in said refuge portion a plurality of refuge plants, said refuge plants being trees of a *paulownia* species;

as said refuge plants grows, pruning said refuge plants so as to limit height and increase leaf density of said refuge plants.

2. The method of claim 1, wherein said crop plants are selected from the group consisting of BT-cotton, BT-corn, and BT-potatoes.

3. The method of claim 1, wherein said planting of said refuge plant further comprises planting each of said plurality of refuge plants within a distance of no greater than 20 feet one from the other.

4. The method of claim 1, wherein said planting of said refuge plant further comprises planting each of said plurality of refuge plants within a distance of no greater than 10 feet one from the other.

5. The method of claim 1, wherein said planting of said refuge plant further comprises planting each of said plurality of refuge plants within a distance of no greater than 4 feet one from the other.

6. The method of claim 1, wherein said planting of said refuge plant further comprises planting each of said plurality of refuge plants within a distance of no greater than 3 feet one from the other.

7. The method of claim 1, wherein said pruning includes cutting back to limit the height of said refuge plants to no greater than 15 feet.

8. The method of claim 1, wherein said pruning includes cutting back to limit the height of said refuge plants to no greater than 10 feet.

9. The method of claim 1, wherein said pruning includes cutting back to limit the height of said refuge plants to no greater than 5 feet.

10. The method of claim 1, wherein said refuge portion of said field is no greater than 10% of said field.

11. The method of claim 1, wherein said refuge portion of said field is no greater than 5% of said field.

12. The method of claim 1, wherein said refuge portion of said field is no greater than 3% of said field.

13. The method of claim 1, wherein said *paulowania* tree is selected from the group consisting of *Paulownia tomentosa, Paulownia elongata, Paulownia fortunei,* and *Paulownia catalpafolia.*

14. The method of claim 1, wherein said pruning comprises cutting a portion of said refuge plants off at ground level so as to permit regrowth from said plants.

15. The method of claim 14, wherein up to 75% of said refuge plants are cut off at ground level.

16. The method of claim 14, wherein up to 50% of said refuge plants are cut off at ground level.

17. The method of claim 1, wherein said larvae is a heliothine larvae.

18. The method of claim 1, wherein said larvae is selected from the group consisting of *Heliothis virescens, Helicoverpa zea, Lepitinotarsa decemlineata, Ostrinaia nubilalis, Spodoptera frugiperda, Pectinophora gossypiella, Diatraea crambidoides, Diatraea grandiosella,* and lepidopteran larvae.

* * * * *